United States Patent [19]

Ishida et al.

[11] Patent Number: 4,803,995
[45] Date of Patent: Feb. 14, 1989

[54] ULTRASONIC LITHOTRITY APPARATUS

[75] Inventors: Akinori Ishida, Kawasaki; Ayao Itoh, Yokohama, both of Japan

[73] Assignee: Kabushiki Kaisha Toshiba, Kawasaki, Japan

[21] Appl. No.: 63,910

[22] Filed: Jun. 19, 1987

[30] Foreign Application Priority Data

Jun. 27, 1986 [JP] Japan .................................. 61-149562
Jul. 22, 1986 [JP] Japan .................................. 61-170834

[51] Int. Cl.$^4$ .............................................. A61B 17/22
[52] U.S. Cl. .............................. 128/660.01; 128/24 A; 128/328
[58] Field of Search ...................... 128/24 A, 328, 660, 128/804

[56] References Cited

U.S. PATENT DOCUMENTS 4,610,499 9/1986 Makofski et al. .................. 128/328
4,617,931 10/1986 Dory .................................. 128/328
4,658,828 4/1987 Dory .................................. 128/660

FOREIGN PATENT DOCUMENTS 0169311 1/1986 European Pat. Off. ............ 128/328

*Primary Examiner*—Ruth Smith
*Attorney, Agent, or Firm*—Oblon, Fisher, Spivak, McClelland & Maier

[57] ABSTRACT

An ultrasonic lithotrity apparatus is held such that its installation position can be adjusted with respect to a stone formed in a living body, and has an ultrasonic lithotrity transducer for emitting an intense ultrasonic wave for breaking up the stone. The ultrasonic lithotrity transducer emits a weak ultrasonic wave immediately before every single or every predetermined number of intense ultrasonic waves is emitted. The position of a stone in the living body can be determined in accordance with a reflected wave of the weak ultrasonic wave. On the basis of reception of the reflected echo signal, the position of the stone is determined. In accordance with the determination result, electronic circuits determine whether the weak or intense ultrasonic wave is to be emitted from the ultrasonic lithotrity transducer.

1 Claim, 4 Drawing Sheets

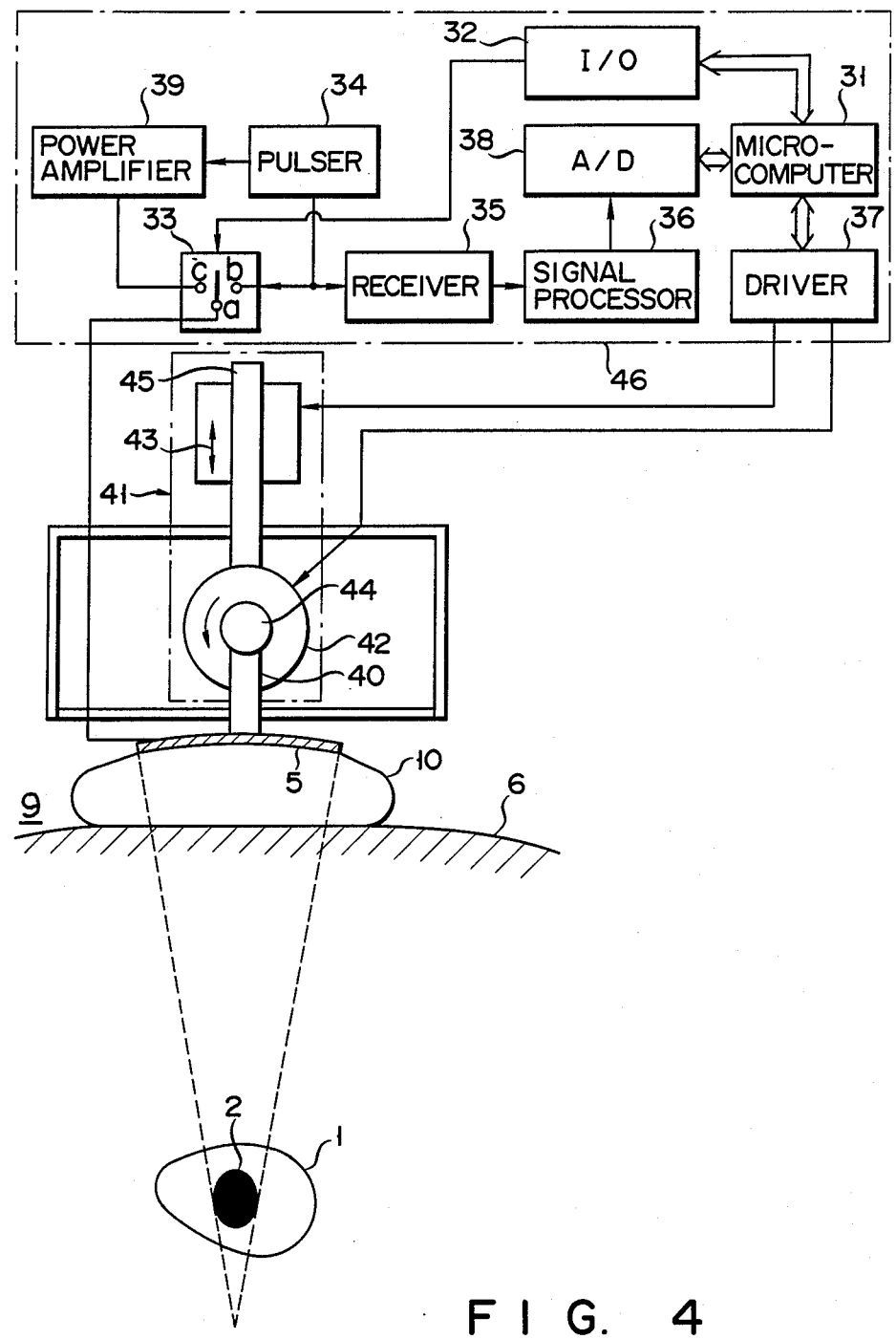
F I G. 4

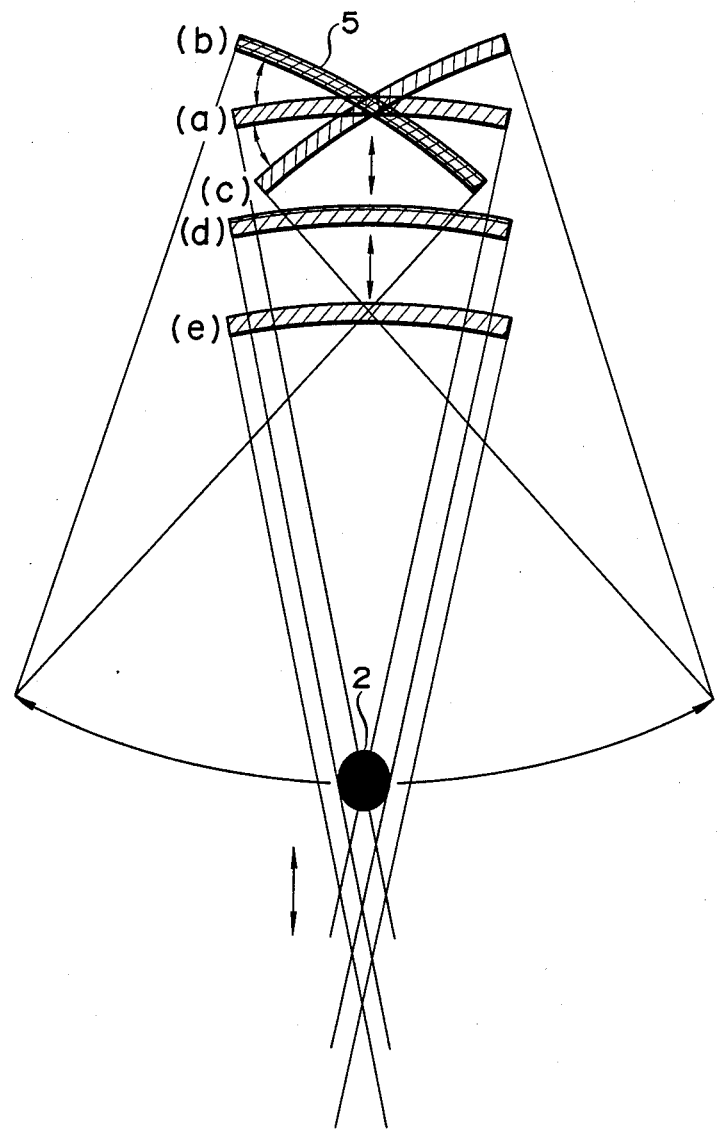
F I G. 5

ULTRASONIC LITHOTRITY APPARATUS

BACKGROUND OF THE INVENTION

The present invention relates to an ultrasonic lithotrity apparatus which is capable of focusing an ultrasonic wave to break up a stone formed in a living body.

An apparatus which breaks up a renal calculus or a gallstone formed in a living body, by externally supplying shock wave energy generated by a discharge or explosion of a powder, is well known, as disclosed in U.S. Pat. No. 3,942,531.

However, as an alternative to the apparatus utilizing shock wave energy, an apparatus for breaking up a stone by means of ultrasonic energy has recently been put into practical use. This apparatus is small in size, can be manufactured at low cost, and can easily determine the presence/absence of a stone.

For example, as is disclosed in U.S. Pat. No. 4,617,931, a well known ultrasonic lithotrity apparatus is constituted by a lithotrity transducer and an image transducer. The lithotrity transducer is concave in shape, forms the focal point of an ultrasonic wave at its geometrical center, and breaks up a stone by focussing emitted ultrasonic energy thereto. The image transducer is used to obtain tomographic image data of a patient; that is, the image of a stone, as part of a tomographic image obtained by the image transducer, is positioned so as to coincide with the geometrical focal point of the lithotrity transducer. After such a coincidence is detected, a wave of intense ultrasonic energy is emitted from the lithotrity transducer and is focused onto the stone, thereby breaking up the stone.

However, when this conventional ultrasonic lithotrity apparatus is used, refraction of an ultrasonic wave is generated on part of the body surface of the patient, or even in the body itself. Therefore, the focal point within the patient, at which an ultrasonic wave emitted from the lithotrity transducer is focused, does not always coincide with the actual position of the stone, as determined by the image transducer. Consequently, the ultrasonic wave is sometimes undesirably focused onto a position other than the actual position of the stone, thereby posing a problem as regards the safety of the patient.

In addition, a stone is rarely broken by only one emission of ultrasonic energy; therefore, ultrasonic energy is normally emitted a number of times. During a series of ultrasonic energy emissions, the patient may sometimes move during repeated operations, with the result, that the focal point of the ultrasonic wave may deviate from the actual position of the stone. Thus, as in the above case, the ultrasonic wave is undesirably focused onto positions other than that of the stone, with possible adverse effects on the patient's health.

SUMMARY OF THE INVENTION

It is therefore an object of the present invention to provide an ultrasonic lithotrity apparatus which is highly safe in use, which can eliminate the above-mentioned drawbacks, and which can detect the position of a stone formed in a patient, detect the focal point of an ultrasonic wave, and align them in relation to each other with a high degree of accuracy, without the risk of adverse effects on living tissue.

In order to achieve the above object of the present invention, an ultrasonic lithotrity apparatus is provided, comprising: an ultrasonic lithotrity transducer for emitting an ultrasonic wave, which forms a focal point; an image ultrasonic transducer for forming an image of a stone in a living body; a holding means for holding both the lithotrity transducer and image ultrasonic transducer such that their installation positions can be adjusted; a driving means for driving the ultrasonic lithotrity transducer so as to emit a weak ultrasonic wave for determining the presence/absence of a stone; a determining means for receiving a reflected wave of the ultrasonic wave from the living body, and determining in accordance with the received wave whether the focal point of the weak ultrasonic wave coincides with the position of the stone; and a driving means, connected to the determining means, and when the determining means determines that the focal point of the weak ultrasonic wave coincides with the stone position, for receiving a determination signal therefrom, and driving the ultrasonic lithotrity transducer to emit the intense ultrasonic wave for breaking up the stone.

According to the ultrasonic lithotrity apparatus of the present invention having the above arrangement, an ultrasonic wave for breaking up a stone is emitted after the presence of a stone is determined, so that the stone can be safely broken up without damaging living tissue.

In addition, since any deviation between the position of the stone and the focal point of the ultrasonic wave is automatically detected, a continuous stonebreaking operation can be reliably and safely performed.

Furthermore, since the position of the stone can be detected by changing the position of an ultrasonic transducer, the stone inside a living body can be accurately and easily broken up.

BRIEF DESCRIPTION OF THE DRAWINGS

FIG. 4 is a block diagram showing an arrangement of another embodiment of the present invention; and FIG. 5 is a schematic view for explaining the movement and sound field area of an ultrasonic transducer shown in FIG. 4.

DETAILED DESCRIPTION OF THE PREFERRED EMBODIMENTS

Figure 1:
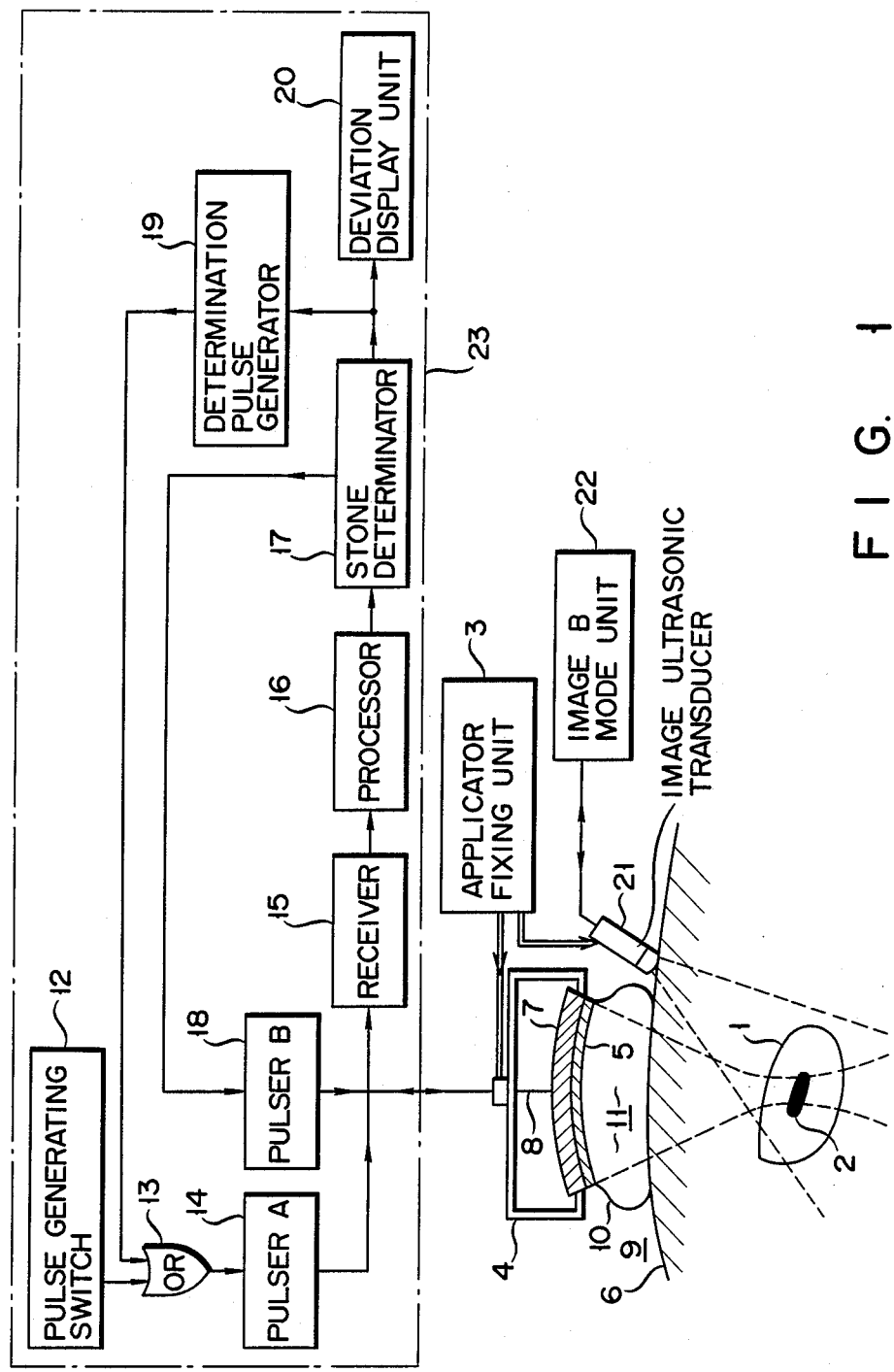
FIG. 1 is a block diagram showing an arrangement of an ultrasonic lithotrity apparatus of the present invention.

An embodiment of the present invention will now be described below, with reference to the accompanying drawings. As is shown in FIG. 1, description will be made with reference to the case wherein renal calculus 2 produced in kidney 1 of a living body is to be broken up.

An ultrasonic lithotrity apparatus of the present invention includes applicator 4 consisting of acoustic coupler 9 which contacts living body surface 6, e.g., the back thereof, concave transducer 5 which operates as an ultrasonic transducer and has a resonant frequency of 500 KHz and a diameter of curvature of 10 cm, and backing member 7 which is adhered to the rear surface of transducer 5. Cable 8 is connected to a pair of electrodes (not shown) provided for transducer 5; and transducer 5 is connected to an external circuit via cable 8. Coupler 9 consists of bag 10 formed by a thin film having an acoustic impedance substantially the same as that of water, and water 11 which fills bag 10. Coupler 9 can efficiently transmit/receive an ultrasonic wave between transducer 5 and the living body. Applicator 4 is positioned by applicator fixing unit 3. This positioning is performed such that the position of renal calculus 2 in a tomographic image obtained by image ultrasonic transducer 21 coincides with the focal point of the ultrasonic wave from transducer 5. Note that image ultrasonic transducer 21 is provided to have a predetermined relative positional relationship with respect to applicator 4. Transducer 21 is positioned by unit 3 and is driven by image B mode unit 22.

External circuit 23 for driving transducer 5 is connected to the pair of electrodes via cable 8. By operating pulse-generating switch 12, circuit 23 supplies a control signal to first pulser 14, through OR gate 13. Pulser 14 generates a pulse signal with a small amplitude, and supplies it to transducer 5. As a result, a weak ultrasonic wave of about 240 mw/cm$^2$ (SPTA (Spatial Peak-Temporal Average intensity) is transmitted from transducer 5 to a diseased part in the living body, through coupler 9. The ultrasonic wave is reflected by the tissue of the living body, received by transducer 5, and converted into an echo signal. Receiver 15 receives the echo signal via cable 8 and supplies it to processor 16. Processor 16 detects only an echo signal reflected by a position near the focal point of the ultrasonic wave transmitted into the living body, and supplies a detection signal to stone determinator 17. Determinator 17 determines the presence/absence of renal calculus 2, in accordance with the received echo signal.

Figure 2:
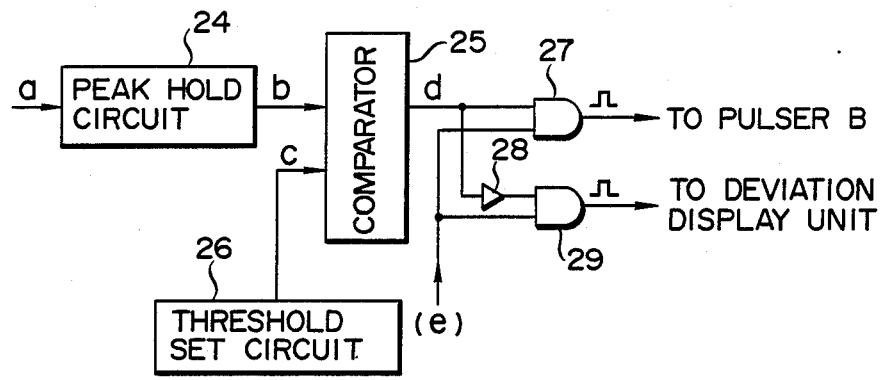
FIG. 2 is a block diagram showing an arrangement of a stone determinator shown in FIG. 1.

FIG. 2 shows an example of a circuit configuration of determinator 17. In FIG. 2, determinator 17 includes peak hold circuit 24 for receiving echo signal a. Output b from circuit 24 is compared in comparator 25 with reference value signal c from threshold-setting circuit 26.

Figure 3:
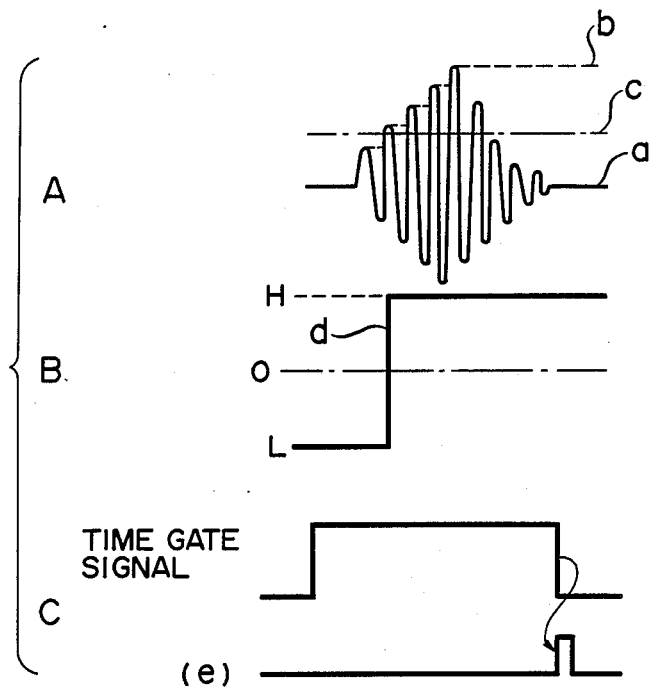
FIGS. 3A to 3C are views of waveforms for explaining an operation of the circuit shown in FIG. 2.

FIG. 3A shows signal a, peak level value b from circuit 24, and level value c of the reference value signal from circuit 25, respectively.

When output d from comparator 25 is at high level, as shown in FIG. 3B, value b is larger than value c (b>c), i.e., a large echo signal is input because of the presence of a renal calculus. This is because the acoustic impedance of the renal calculus is larger than that of living tissue.

When a renal calculus is not present, a low level value of FIG. 3B is obtained as output d (b<c).

Output d from comparator 25, together with time gate signal e, are supplied to AND gate 27. Output d is also supplied, together with signal e, to AND gate 29, via inverter 28.

When output d is at high level, an output is obtained from AND gate 27 and is supplied as a control signal to pulser 18, shown in FIG. 1. That is, when determinator 17 determines that a stone is present, a drive control signal is supplied to pulser 18, and pulser 18 supplies a pulse signal with a large amplitude to transducer 5 via cable 8. As a result, transducer 5 emits an intense ultrasonic wave, for breaking up a stone, with a peak power of, for example, 100 KW or more, onto renal calculus 2 in the living body, thereby breaking renal calculus 2 positioned at the focal point of the wave.

On the other hand, when determinator 17 determines that a stone is not present, no control signal is supplied to pulser 18, and the ultrasonic wave is not emitted. Determination signals indicating that no stone is present are supplied as low-level signals from gate 29, shown in FIG. 2, to determination pulse generator 19 and deviation display circuit 20. Generator 19 generates a determination pulse and supplies it again as a control signal to pulser 14, through OR gate 13. Transducer 5 emits the ultrasonic wave onto renal calculus 2, and repeats this operation a number of times. When circuit 20 receives three consecutive determination signals indicating that a stone is not present, it is concluded that the apparent absence of a stone is caused not because of minor movements to due breathing by the body, but because there is a large deviation of the positions between a stone and a focal point of the ultrasonic wave. Therefore, an operator operates unit 3 to move applicator 4 to a new position. Thus, the intense ultrasonic wave for breaking up a stone can be emitted after the presence of a renal calculus has been determined, so that only the stone will be broken up, and no damage caused to living tissue. A weak ultrasonic wave is emitted from transducer 5, so as to determine the presence/absence of a renal calculus, in accordance with the control signal from pulser 14. This weak ultrasonic wave may be emitted immediately before every signal or every predetermined number of intense ultrasonic waves is emitted.

Another embodiment of the present invention will now be described, with reference to FIGS. 4 and 5. In this embodiment, the position of a stone is determined by moving an ultrasonic transducer. After the positioning procedure has been accurately performed, an intense ultrasonic wave is emitted, thereby breaking up the stone, without damaging living tissue.

For example, in order to break up renal calculus 2 in kidney 1, concave transducer 5, which operates as an ultrasonic transducer and has a resonant frequency of, for example, 500 KHz, is positioned on living body surface 6, by means of acoustic coupler 9. Transducer 5 is supported by shaft 40 and is coupled to driving mechanism 41. Mechanism 41 includes sector scanner 42 and vertical driver 43. Scanner 42 is pivotally supported by shaft 44, so as to sector-scan transducer 5 along a left-to-right direction. Vertical driver 43 holds transducer 5 and scanner 42 by means of shaft 45, so as to move them vertically. Scanner 42 and vertical driver 43 are driven in accordance with a control signal from driver 37 of electronic circuit 46. Circuit 46 includes microcomputer 31. Switch 33 first receives an instruction signal from microcomputer 31, via I/O buffer 32, and its contacts a and b are connected to each other. A pulse with a small amplitude is supplied from pulser 34 to transducer 5, via switch 33, and a weak ultrasonic pulse is emitted from transducer 5 to a stone formed in a living body, and is reflected thereby. A reflected ultrasonic echo is received by transducer 5 and is amplified by receiver 35 via switch 33. Thereafter, an envelope of the echo signal is obtained by signal processor 36. At this time, microcomputer 31 supplies a driving pulse to scanner 42, via driver 37. As a result, pivotal movement of shaft 44 is transmitted to transducer 5, which then emits the ultrasonic wave at different angles according to different positions, in the order or positions (a)→(b)-→(a)→(c)→(a) as shown in FIG. 5. Every time transducer 5 changes its angle, the ultrasonic wave is repeatedly transmitted/received against the stone, and envelopes of the ultrasonic echoes are acquired by microcomputer 31, via switch 33, receiver 35, signal processor 36, and A/D converter 38. An angle of inclination, i.e., the position of transducer 5, obtained when the ultrasonic echo is the maximum and the magnitude of its echo signal are stored in microcomputer 31. The detection of the maximum echo signal means that the presence of stone in the living body has been determined. Subsequently, microcomputer 31 instructs driver 37 to drive vertical driver 43, thereby vertically moving the position of transducer 5, in the order of positions (a)→(d)→(e)→(d)→(a) as shown in FIG. 5, by means of shaft 45 and scanner 42. As has been described above, the ultrasonic wave is transmitted/received every time transducer 5 moves, and microcomputer 31 stores the maximum echo signal and the position of transducer 5 at that time.

Thus, the position of a stone in the living body can be determined with high accuracy. Then, microcomputer 31 drives switch 33, via I/O 32, thereby connecting contacts a and c with each other. As a result, an output from pulser 34 is amplified by power amplifier 39, and is supplied to transducer 5. Transducer 5 emits the intense ultrasonic wave onto the stone formed in the living body, and the stone is broken up.

As has also been described above, the position of a stone is determined with high accuracy, after which the ultrasonic wave for breaking up the stone is emitted. Therefore, the stone is safely broken up, without damage to body tissue.

Note that the present invention is not limited to the above embodiments, but can be variously modified without departing from the spirit and scope of the invention.

What is claimed is:

1. An ultrasonic lithotrity apparatus comprising:
   first ultrasonic transducer means for forming an image in a living body;
   second ultrasonic transducer means for emitting and receiving an ultrasonic wave which forms a focal point to break up a stone;
   adjusting means for adjusting both positions of said first and second ultrasonic transducer means such that a position of the focal point of the ultrasonic wave coincides with the position of the stone;
   first driving means for driving said second ultrasonic transducer means to emit an ultrasonic wave for determining the presence/absence of said stone at the focal point;
   determining means for receiving, from said second ultrasonic transducer means, a reflected wave of the ultrasonic wave from the living body, and determining in accordance with the received wave whether the focal point of the ultrasonic wave coincides with the position of said stone; and
   second driving means, connected to said determining means, and when said determining means determines that the focal point of the ultrasonic wave coincides with the position of said stone, for receiving a determination signal therefrom and driving said second ultrasonic transducer means to emit an ultrasonic wave for breaking up said stone, the intensity ($w/cm^2$) of the ultrasonic wave for breaking up said stone being different from the intensity ($w/cm^2$) of the ultrasonic wave for determining the presence/absence of said stone.

* * * * *